United States Patent [19]

Cordy

[11] Plant 4,148

[45] Nov. 15, 1977

[54] PEAR TREE

[75] Inventor: Clifford B. Cordy, Central Point, Oreg.

[73] Assignee: Naumes of Oregon, Inc., Medford, Oreg.

[21] Appl. No.: 684,797

[22] Filed: May 10, 1976

[51] Int. Cl.[2] ..... A01H 5/03

[52] U.S. Cl. ..... Plt./36

[58] Field of Search ..... Plt./36

*Primary Examiner*—Robert E. Bagwill

*Attorney, Agent, or Firm*—Kolisch, Hartwell, Dickinson & Stuart

[57] ABSTRACT

This new variety of pear is primarily distinguished by its dark red fruit with flesh free of grit cells.

2 Drawing Figures

This discovery relates to a new and distinctive variety of pear tree.

A particularly distinguishing feature of the new variety of pear tree is the distinctive coloring and shape of the fruit. The pear at picking time and when ready for eating has a deep reddish coloring with a somewhat golden underlying background and small pores. The meat of the pear is very smooth, having little or no grit cells or grittiness.

The distinctive coloring and shape of the pear increases its marketability, as the coloring is appealing and attractive to buyers.

Accompanying this specification are two color photographs numbered FIGS. 1 and 2 illustrating in color the new variety of pear.

Figure 1:
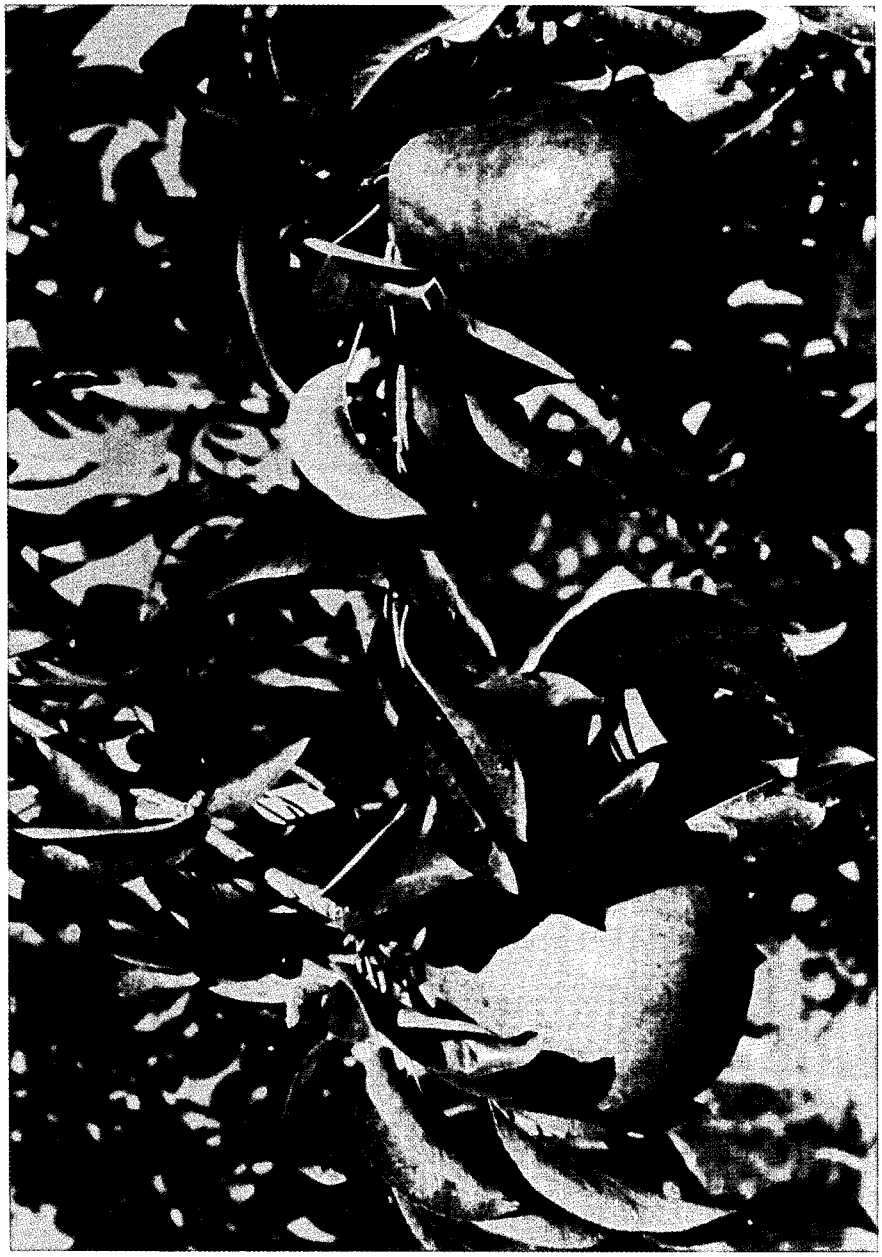
FIG. 1 is a view of two of the new pears as they appear on a tree, with the pear at the right in the figure in a cleaned and polished state, and the pear at the left in the figure being covered with natural waxes and sprays.
Figure 2:
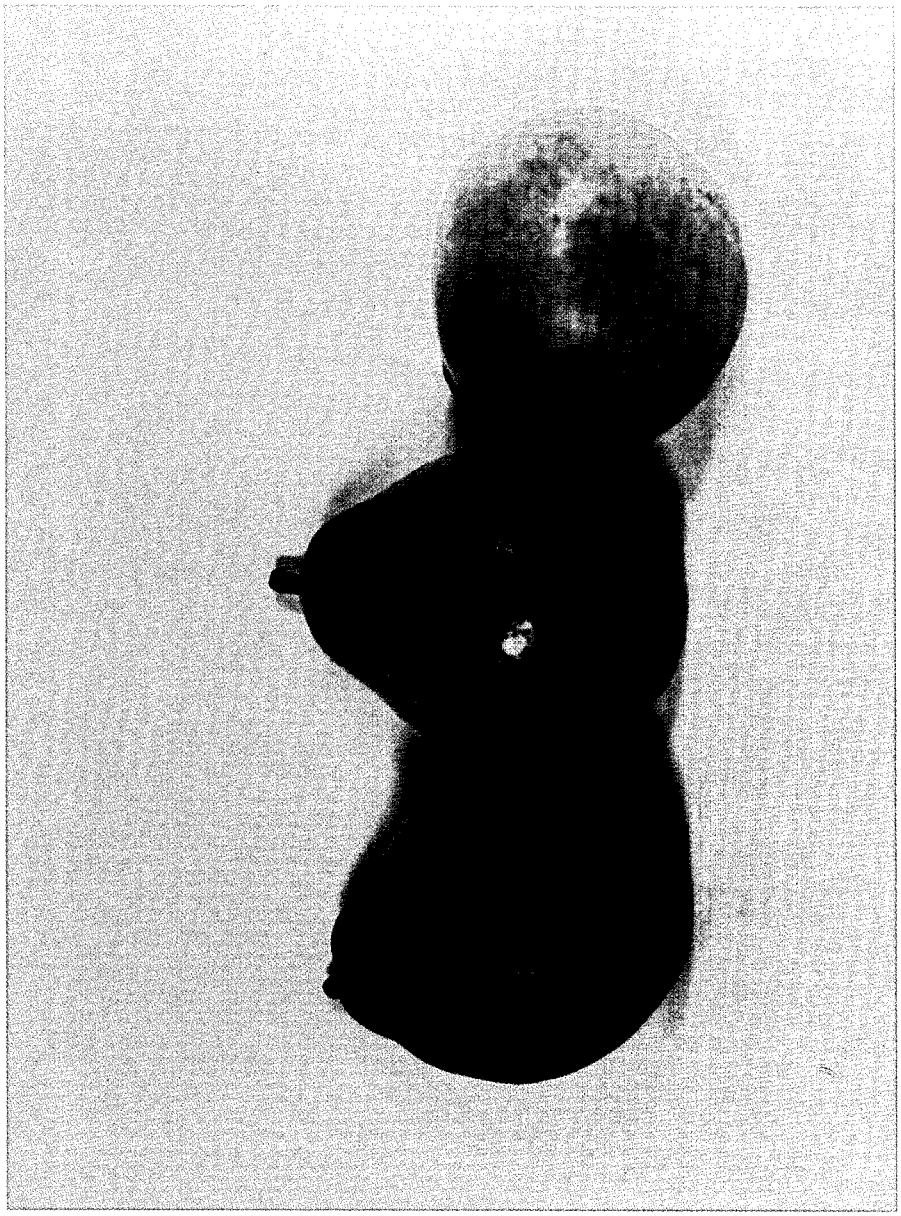
FIG. 2 is a photograph of three pears removed from the tree illustrating the general shape and coloration of the pear.

The pear tree was discovered and asexually reproduced in a cultivated area in the County of Jackson, Oreg. in the vicinity of Medford, Oreg. Asexual reproduction was by grafting, such grafting illustrating that the distinctive features of the pear was established and transmitted through succeeding propagations.

The new pear tree was developed by crossing Red Bartlett with Green Anjou. One new variety which resulted from the crossing of the parent Red Bartlett and Anjou is the subject of this application.

The new variety is probably most similar to its parent Red Bartlett. The leaves of the new variety are narrower, longer and less serrated than the Bartlett. The flowers of the new variety are smaller than the Bartlett. The anther of the new variety is purple, whereas the Bartlett is pink. The fruit of the new variety has a skin which is more tender than its parent Bartlett, and its flesh is free of grit cells, whereas the Bartlett and the Anjou have grit cells. The new variety is free of pubescence when the blossom petals fall, whereas the Bartlett evidences pubescence generally for three weeks after the petals fall. The fruit of the new variety is less pyriform than the Bartlett, and is between the Bartlett and Anjou in shape. Generally the Bartlett has a length to diameter ratio of approximately 1.5 to 1, the Anjou has a ratio of 1.25 to 1, approximately, whereas the new variety has a length to diameter ratio between these two ratios recited for the Bartlett and Anjou.

The new variety has a generally overall dark red color with a golden undercolor. The red Bartlett does not have as golden a background and may have green streaks at times due to reversion to the original green, which is not found in the new variety.

Below there appears a detailed description of the new variety of pear tree, such description being based upon observations of pear specimens and with reference to botanical authorities. The predominant color identified for the pear was identified with reference to colors designated in Robert Ridgway's "Colors Standards and Nomenclature" (1912).

Tree: Large; vigorous; spreading; tall; open; rapid growing; hearty; productive.

*Branches.*—Medium thickness, relatively smooth and gray with medium number and medium sized lenticels.

*Leaves.*—Are substantially medium in length and width, ovate and taper-pointed, of medium thickness, being light in color on the underside and dark green on the upperside, with the leaves being substantially smooth and folded or recurved. The leaves are approximately 2½ to 3½ inches long and 1½ to 2 inches in width. The margins are crenate; petiole approximately ¾ to 1¾ inches long and of medium thickness.

*Flowers.*—Small, pink and sterile. The blooming date in Medford, Oreg. in 1974 was Apr. 10 and in 1975 was Apr. 20–28.

Fruit: Good keeping quality, in good condition at end of December, and has good resistance to insects. The length of the season from early full bloom to start of the harvest averages 150 to 165 days. The date of ripening in 1974 was September 10 and in 1975 was September 24. The later 1975 season was due to differing weather conditions in this region in 1975. The fruit hangs well.

*Size.*—Large, uniform oblong shape with sides being somewhat unequal. The fruit of the new variety may be from 2 inches to over 3 inches in diameter.

*Stem.*—Of medium thickness and approximately ½ to ¾ inch long.

*Cavity.*—Is acute, of medium depth and width. The cavity is russeted, symmetrical and lipped.

*Calyx.*—Is small and closed.

*Lobes.*—Are short, narrow, acute, and separated at the base.

*Basin.*—Is shallow, narrow, obtuse, smooth and furrowed.

*Skin.*—Is thin, smooth, waxen and bloom.

*Color.*—Is generally an overall dark red color with a golden under color. Color identification with reference to the color authority noted above showed the dominant coloration to be between a Brazil red and Morocco red with slight gold undertones.

*Dots.*—Numerous, medium in size, gray and areolar.

*Flesh.*—White, fine, tender, and juicy to sweet.

*Core.*—Small, closed and axile.

*Corelines.*—Clasping.

*Calyx tube.*—Long and narrow.

*Seeds.*—Medium in size, flat and acuminate.

What is claimed is:

1. A new and distinct variety of pear tree, substantially as shown and described herein, distinguished by the physical characteristics of the fruit including its shape and overall dark red coloration of the fruit skin.

* * * * *